(12) United States Patent
Seth et al.

(10) Patent No.: US 7,748,090 B2
(45) Date of Patent: Jul. 6, 2010

(54) BREATHABLE FASTENERS

(75) Inventors: Jayshree Seth, Woodbury, MN (US); Ronald W. Ausen, St. Paul, MN (US); James S. Mrozinski, Oakdale, MN (US); Janet A. Venne, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/612,082

(22) Filed: Dec. 18, 2006

(65) Prior Publication Data

US 2007/0089279 A1   Apr. 26, 2007

Related U.S. Application Data

(62) Division of application No. 10/602,385, filed on Jun. 24, 2003, now Pat. No. 7,168,139.

(51) Int. Cl.
   *A44B 18/00* (2006.01)
(52) U.S. Cl. .................................................. 24/452
(58) Field of Classification Search ............ 24/442, 24/450, 452, 16 R, 16 PB; 604/391; 428/100
   See application file for complete search history.

(56) References Cited

U.S. PATENT DOCUMENTS

| | | | |
|---|---|---|---|
| 3,138,841 A | 6/1964 | Naimer | |
| 4,290,174 A | 9/1981 | Kalleberg | |
| 4,454,183 A | 6/1984 | Wollman | |
| 4,539,256 A | 9/1985 | Shipman | |
| 4,726,989 A | 2/1988 | Mrozinski | |
| 4,777,073 A | 10/1988 | Sheth | |
| 4,814,124 A | 3/1989 | Aoyama et al. | |
| 4,894,060 A | 1/1990 | Nestegard | |
| 5,077,877 A | 1/1992 | Piotrowski | |
| 5,315,740 A | 5/1994 | Provost | |
| 5,551,130 A | 9/1996 | Tominaga et al. | |
| 5,607,635 A | 3/1997 | Melbye et al. | |
| 5,679,302 A | 10/1997 | Miller et al. | |
| 5,791,969 A | 8/1998 | Lund | |
| 5,845,375 A | 12/1998 | Miller et al. | |
| 5,879,604 A | 3/1999 | Melbye et al. | |
| 5,997,981 A | 12/1999 | McCormack et al. | |
| 6,195,850 B1 * | 3/2001 | Melbye et al. | ............... 24/304 |
| 6,287,665 B1 | 9/2001 | Hammer | |
| 6,368,097 B1 | 4/2002 | Miller et al. | |
| 6,506,175 B1 | 1/2003 | Goldstein | |
| 6,558,602 B1 | 5/2003 | Melbye et al. | |
| 6,568,047 B2 | 5/2003 | Murasaki | |
| 7,168,139 B2 | 1/2007 | Seth et al. | |
| 2001/0018110 A1 | 8/2001 | Tuman et al. | |
| 2004/0258902 A1 | 12/2004 | Seth | |

FOREIGN PATENT DOCUMENTS

| | | |
|---|---|---|
| EP | 0 510 998 | 10/1992 |
| WO | WO 01/32403 A1 | 5/2001 |
| WO | WO 01/43969 A1 | 6/2001 |
| WO | WO 01/45609 A1 | 6/2001 |

\* cited by examiner

*Primary Examiner*—James R Brittain

(57) ABSTRACT

The present invention concerns breathable fasteners for use with hook fastener systems. The breathable fastening system comprises a first breathable mechanical fastener surface, which is generally a loop or fibrous type surface that can optionally be joined to a breathable backing loop, and a recon large area breathable hook type fastener. The hook type fastener generally has an integral film backing which film backing has a porosity of from 0.0001 to 0.005 cm$^3$, a backing thickness of from 25 to 200 μm, a stiffness of from 10 to 2000 Gurley units and a hook or projection containing surface area of at least 10 cm$^2$.

9 Claims, 3 Drawing Sheets

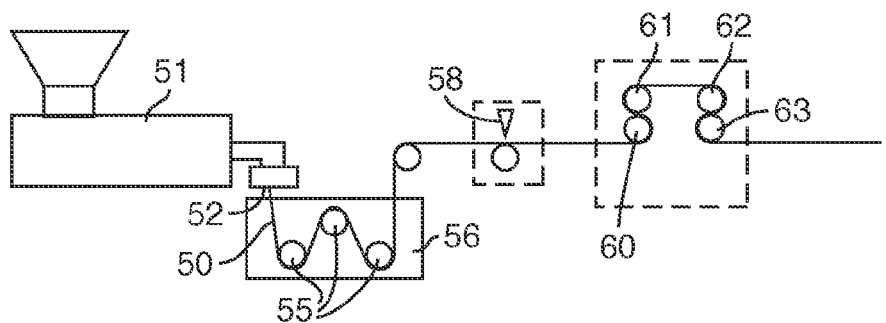
Fig. 1
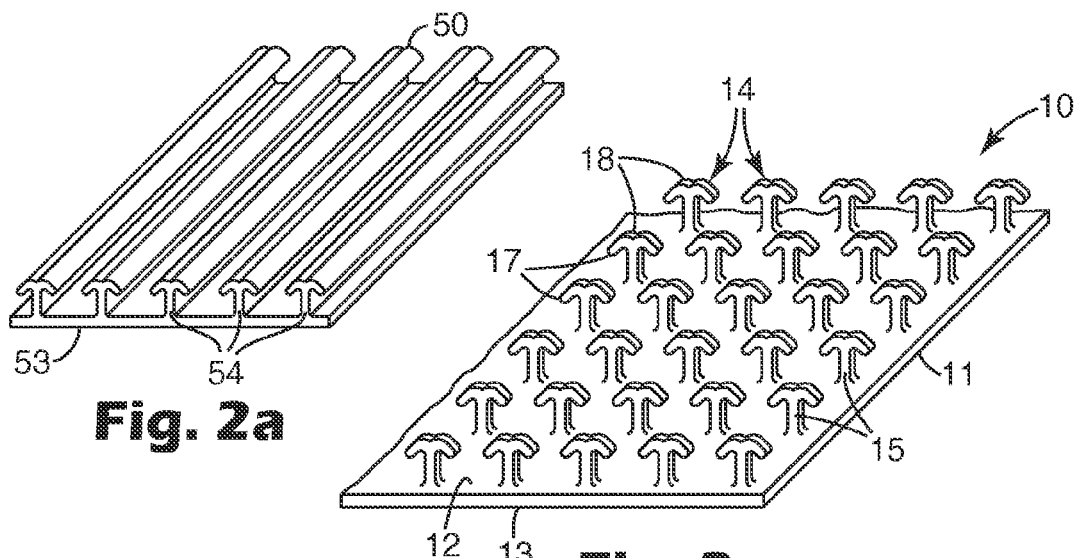
Fig. 2a
Fig. 2c
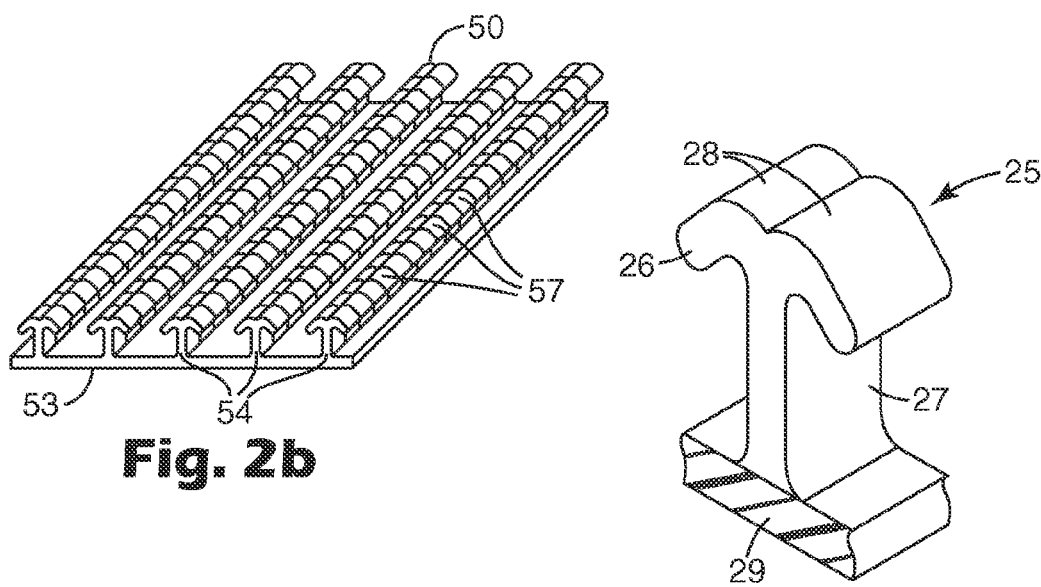
Fig. 2b
Fig. 2d

BREATHABLE FASTENERS

CROSS REFERENCE TO RELATED APPLICATIONS

This application is a divisional of U.S. Ser. No. 10/602,385, filed Jun. 24, 2003, now U.S. Pat. No. 7,168,139, the disclosure of which is incorporated by reference in its entirety herein.

BACKGROUND AND SUMMARY

The present invention concerns breathable hook fasteners.

BACKGROUND OF THE INVENTION

Disposable absorbent articles, namely diapers, adult incontinent articles and feminine hygiene pads have recently been designed with breathable outer layers to increase the comfort of the wearer. PCT Publication No. WO01/45609 proposes forming a liquid impermeable and breathable outer cover sheet for a disposable garment formed of a meltblown nonwoven web. PCT Publication No. WO01/32403 proposes a breathable multilayer elastic film for use as a disposable absorbent article outer cover sheet and PCT Publication No. WO01/43969 also discloses a laminate of breathable film and a nonwoven for use as a backing for a diaper and the like. This patent document states that breathable laminates of a stretched porous film and a nonwoven, such as spunbond webs, are commonly used in diapers stating laminates which are breathable to water vapor but substantially impermeable to liquid water are known in the art, and are commonly used in diaper backings, other personal care absorbent garments, medical garments and the like. These laminates may be composed of a breathable, stretch-thinned filled film and a spun bond web. The breathable film can be formed by blending one or more polyolefins with an inorganic particulate filler, forming a film from the mixture, and stretching the film to cause void formation around the filler particles. The resulting film may have thin polymer membranes around the filler particles which permit molecular diffusion of water vapor, while the overall film substantially blocks transmission of liquid water, or may have micropores going through the film. The breathable film can be laminated to a nonwoven web, for instance, a spunbond web, by thermal, adhesive, pressure or ultrasonic, or combinations thereof. The spunbond web adds strength and integrity to the breathable laminate, and provides a soft, cloth-like feel.

Another trend in the disposable absorbent article industry is the use of hook and loop type mechanical fastening systems. Hook fasteners are generally fairly small and engage a large area loop patch on the diaper or the like. The loop patch in order not to compromise the breathability of the diaper is also generally preferably breathable or air permeable. The hook element, however, has not been breathable. However, as hook patches become larger, it is desirable to provide disposable, thin, conformable hook fasteners that can both function effectively as a hook and also be breathable. Breathability or air permeability promotes skin health by allowing air to circulate next to the skin.

There are a variety of methods known to form hook materials for hook and loop fasteners. One of the first manufacturing methods for forming hooks involved weaving loops of monofilaments into a fibrous or film backing or the like followed by cutting the filament loops to form hooks. These monofilament loops were also heated to form headed structures such as disclosed in U.S. Pat. Nos. 4,290,174; 3,138,841 or 4,454,183. These woven hooks are generally durable and work well for repeated uses and are breathable. However, they are generally expensive and coarse to the touch.

For use in disposable garments and the like, it is generally desirable to provide hooks that are inexpensive and less abrasive. For these uses and the like, the solution is generally the use of continuous extrusion methods that simultaneously form a backing and the hook elements, or precursors to the hook elements. With direct extrusion molding formation of the hook elements, see for example U.S. Pat. No. 5,315,740, the hook elements must continuously taper from the backing to the hook tip to allow the hook elements to be pulled from the molding surface. Alternatively, stem-like shapes can be directly molded and subsequently modified into a hook such as disclosed, for example, in U.S. Pat. Nos. 5,077,877; 6,558,602; 6,368,097 or 5,679,302. An alternative direct extrusion process is proposed, for example, in U.S. Pat. No. 4,894,060, which permits the formation of hook elements without these limitations. Instead of the hook elements being formed as a negative of a cavity on a molding surface, the basic hook cross-section is formed by a profiled extrusion die. The die simultaneously extrudes the film backing and rib structures. The individual hook elements are then formed from the ribs by cutting the ribs transversely followed by stretching the extruded strip in the direction of the ribs. The backing elongates but the cut rib sections remain substantially unchanged. This causes the individual cut sections of the ribs to separate each from the other in the direction of elongation forming discrete hook elements. Alternatively, using this same type extrusion process, sections of the rib structures can be milled out to form discrete hook elements. With all these methods, the hooks are relatively inexpensive but not breathable. The hook fastener is mated to a breathable mating fastener surface which generally is a breathable loop fastener.

BRIEF DESCRIPTION OF THE INVENTION

The present invention is directed at providing a breathable or porous, conformable large area fastener element for use in disposable absorbent articles and like articles. The fastener is preferably a unitary polymeric hook fastener comprising a thin, strong flexible breathable film backing, and a multiplicity of integral spaced hook members projecting from at least one major surface of the unitary breathable backing. The invention further relates to a method for forming a unitary breathable polymeric film backed hook fastener. The fastener and the method of the invention forms upstanding projections, which may or may not be hook members that project upwardly from a major surface of a unitary breathable film backing of at least a uniaxially oriented polymer. The fastener members if hook fasteners each comprise at least a stem portion attached at one end to the film backing, and preferably a head portion at the end of the stem portion opposite the backing to allow for more secure engagement with a loop type material. A head portion can also extend from a side of a stem portion. The head portion preferably projects past the stem portion on at least one of two opposite sides. Conformable breathable fasteners of the invention generally comprise a two-dimensional fastener of a surface area of greater than 10 $cm^2$ up to 100 $cm^2$ or more, preferably greater than 20 $cm^2$ up to 70 $cm^2$, which can be in the form of a rectilinear fastener, or preferably a complex body conforming shape having at least one curved surface for engaging the contour of a wearer. The large area breathable fastener is used alone or as a laminate with a further breathable layer such as a nonwoven web and engaged with a mating breathable mechanical fastening surface.

BRIEF DESCRIPTION OF THE DRAWINGS

The present invention will be further described with reference to the accompanying drawings wherein like reference numerals refer to like parts in the several views, and wherein:

FIG. 1 schematically illustrates a method for making the hook fastener of FIGS. 2a-2d.

FIGS. 2a, 2b and 2c illustrate the structure of hook fastener at various stages of its processing in the method illustrated in FIG. 1.

FIG. 2d is an enlarged perspective view of a hook fastener of FIG. 2c.

DETAILED DESCRIPTION OF THE PREFERRED EMBODIMENTS

Figure 3:
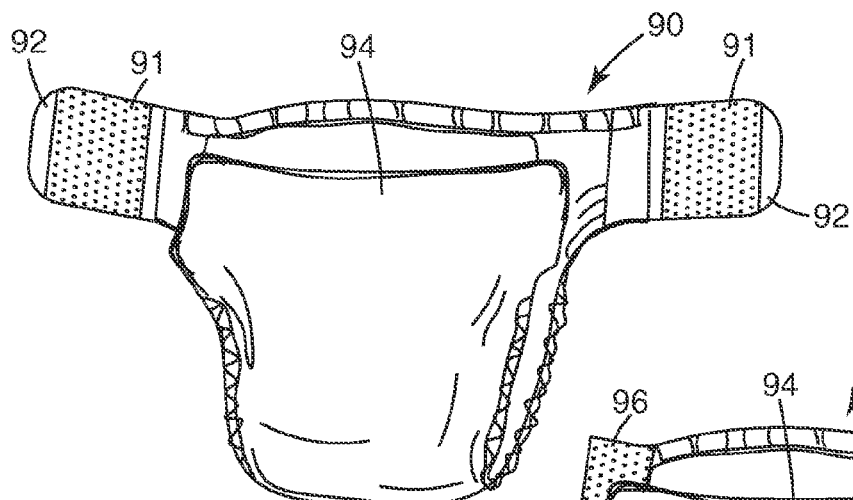
FIG. 3 is a perspective view of a disposable garment using a breathable hook fastener member according to the present invention.

The present invention mechanical fastener has a porous film-like backing of a thermoplastic material that is generally a porous stretched or oriented fastener made of a thermoplastic material. The porosity of the interstitial volume per unit area of the porous film material of the mechanical fastener is preferably in the range of 0.0001-0.005 cm$^3$ as calculated by the equation:

Interstitial volume per unit area=[film thickness (cm)×1 (cm)×1 (cm)×void content (%)]/100 (where the void content is the percentage of voids in the porous film).

The porous stretched fastener may be produced by various different methods using a thermoplastic material as the starting substance. In one preferred method, the film backed fastener is produced by adding a diluent to a transparent crystalline thermoplastic resin, forming a film backed fastener using conventional methods, and then stretching the formed fastener to create fine voids therein. A porous stretched thermoplastic fastener obtained in this manner has a large percentage of voids constituting a volume of the fastener backing. The thermoplastic film backing has a structure with a substantially uniform distribution of many fine voids. Examples of preferred transparent crystalline thermoplastic resins which can be used as the film forming material for production of the porous unstretched thermoplastic fastener of the invention include, but are not limited to, polyethylene, polypropylene, polybutylene, poly-4-methylpentene and ethylene-propylene block copolymer.

Examples of preferred nonparticulate diluents that can be used in combination with the aforementioned thermoplastic resins to provide the fine voids include, but are not limited to, mineral oils, petroleum jelly, low molecular weight polyethylene, soft Carbowax and mixtures thereof. Mineral oils are preferred among these diluents because of their relatively low cost. The diluents may optionally be partially on entirely extracted from the films by known methods. However, additionally conventional particulate based fillers can also be used to form the porous film, such as talc, calcium carbonate, titanium dioxide, barium sulfate, etc.

The aforementioned fillers or diluents can be varied within a wide range within the starting thermoplastic resin used for production of the film backed fastener. The amount of filler or diluents used is preferably in the range of 20-60% by weight, and more preferably 25-40% by weight of the starting thermoplastic material. If the amount of filler or diluent added to the starting material is under 20% by weight, the void content of the hook film resulting after stretching is reduced, while if it is above 60% by weight it becomes more difficult to produce flexible coherent film backed fasteners.

Other additives may also be added as necessary in addition to the thermoplastic resin and filler or diluent in the production of the porous stretched thermoplastic fastener. For example, organic acids such as carboxylic acid, sulfonic acid and phosphonic acid, and organic alcohols. As additional suitable additives there may also be mentioned, for example, inorganic and organic pigment, aromatic agents, surfactants, antistatic agents, nucleating agents and the like.

The main starting materials and optional additives are melted and/or combined producing a filler-containing thermoplastic fastener. The melting and mixing step(s) and the subsequent fastener element or hook forming step may be carried out according to known methods, but modified to ensure formation of a porous backing for the fastener. An example of a suitable melt mixing method is kneading with a kneader, and examples of suitable hook forming methods are extrusion and extrusion molding or casting methods. The mold casting method can give films by melt mixing the main starting material, etc. and then extruding it from a die onto a cavity containing roll (e.g., preferably a cold roll). The cavities directly form the hooks or hook precursor that could subsequently be applied on otherwise modified to form a hook such as by the application of heat. Examples of such methods are disclosed in U.S. Pat. Nos. 5,077,870; 5,607,635; 5,879,604; 6,558,602; 5,679,302; 5,845,375; 6,287,665; 6,568,047; 5,551,130 or 5,791,969, the substance of which are incorporated by reference in their entirety. The direct extrusion method forms projections or hook precursors directly from a die. In a modified forms of these methods, the nonparticulate additives and/or fillers may be removed by washing off or extracting with a suitable solvent after extrusion of the melted mixture.

The formed filler-containing thermoplastic fastener material is then preferably stretched sufficiently to provide it with fine voids in the film backing. The stretching may be carried out according to known methods, such as uniaxial stretching or biaxial stretching. For example, in the case of biaxial stretching, the stretching in the lengthwise direction may be accomplished by varying the speed of the driving roll, and the stretching in the widthwise direction may be accomplished by mechanical pulling in the widthwise direction while holding both sides of the fastener with clips or clamps.

The conditions for the fastener stretching are not particularly restricted, but the stretching is generally carried out so as to give a stretched fastener backing thickness in the range of 25-500 μm. The backing of the hook fastener must be thick enough to allow it to be attached to a substrate by a desired means such as sonic welding, heat bonding, sewing or adhesives, including pressure sensitive or hot melt adhesives, and to firmly anchor the stems and provide resistance to tearing when the fastener is peeled open, or placed under shear. However, when a fastener is used on a disposable garment, the fastener backing should not be so thick that it is stiffer than necessary. Generally, the fastener backing has a Gurley stiffness of 10 to 2000, preferably 10 to 200 so as to allow it to be perceived as soft when used either by itself or laminated to a further carrier backing structure such as a nonwoven, woven or film-type backing, which carrier backing should also be similarly soft for use in disposable absorbent articles. Softness is preferred such that the fastener can conform to the contours of a wearer's body. The optimum backing thickness will vary depending upon the resin from which the hook fastener is made, but is preferably 50 to 150 μm for softer backings.

The stretching ratio for the thermoplastic fastener is usually preferred to be in the range of 1.5 to 3.0 in one or both of the longitudinal and transverse directions. If the stretching ratio is under 1.25 it becomes difficult to achieve a sufficient void content, while if it is over 3.0 the voids tend to collapse and/or the fastener backing breaks. The average size of the voids in the fastener backing formed by stretching of the fastener is usually preferred to be in the range of 0.2 to 2 μm.

As mentioned above, the interstitial volume per unit area or porosity of the porous stretched thermoplastic fastener backing obtained by the stretching process described earlier is preferably in the range of 0.0001-0.005 $cm^3$, and more preferably in the range of 0.0002-0.001 $cm^3$, as calculated by the equation defined above.

Referring now to FIG. 2c is an exemplary polymeric hook type fastener, which can be produced according to the present invention by a direct extrusion method, is generally designated by the reference numeral 10. The hook fastener 10 comprises a thin strong flexible film-like backing 11 having generally parallel upper and lower major surfaces 12 and 13, and a multiplicity of spaced hook members 14 projecting from at least the upper surface 12 of the backing 11. The backing can have planar surfaces or surface features as could be desired for tear resistance or reinforcement. As is best seen in FIG. 2d, the hook members 25 each comprise a stem portion 27 attached at one end to the backing 29 and preferably having tapered sections that widen toward the backing 29 to increase the hook anchorage and breaking strengths at their junctures with the backing 29, and a head portion 26 at the end of the stem portion 27 opposite the backing 29. The sides of the head portion 26 can be flush with the sides of the stem portion on two opposite sides. The head portion 26 has hook engaging parts or arms 28 projecting past the stem portion 27 on one or both sides.

A first embodiment preferred method for forming a porous or breathable hook fastener, such as that of FIG. 2d, is schematically illustrated in FIG. 1. Generally, the method includes first directly extruding a strip 50 shown in FIG. 2 of thermoplastic resin from an extruder 51 through a die 52 having an opening cut, for example, by electron discharge machining, shaped to form the strip 50 with a base 53 and elongate spaced ribs 54 projecting above an upper surface of the base layer 53 that have the cross sectional shape of the hook portions or members to be formed. The strip 50 is pulled around rollers 55 through a quench tank 56 filled with a cooling liquid (e.g., water), after which the ribs 54 (but generally not the base layer 53) are transversely slit or cut at spaced locations along their lengths by a cutter 58 to form discrete portions 57 of the ribs 54 having lengths corresponding to about the desired thicknesses of the hook portions to be formed, as is shown in FIG. 2d. The cut can be at any desired angle, generally from 90° to 30° from the lengthwise extension of the ribs. Optionally, the strip can be stretched prior to cutting to provide further molecular orientation to the polymers forming the ribs and/or reduce the size of the ribs and the resulting hook members formed by slitting of the ribs. The cutter 58 can cut using any conventional means such as reciprocating or rotating blades, lasers, or water jets, however preferably it cuts using blades oriented at an angle of about 60 to 80 degrees with respect to the lengthwise extension of the ribs 54.

After cutting of the ribs 54, the base 53 of the strip 50 is longitudinally stretched at a stretch ratio of at least 1.5 to 1, preferably between a first pair of nip rollers 60 and 61 and a second pair of nip rollers 62 and 63 driven at different surface speeds. Optionally, the strip 50 can also be simultaneously or sequentially transversely stretched to provide biaxial orientation to the base 53. Roller 61 is preferably heated to heat the base 53 prior to stretching, and the roller 62 is preferably chilled to stabilize the stretched base 53. Stretching causes spaces between the cut portions 57 of the ribs 54, which then become the hook portions or members 14 for the completed hook fastener portion 10. A hook density of at least 50 and preferably from 70 to 150, up to 300 hooks per square centimeter is best suited for the invention breathable hook fastener for most conventional loop fasteners. The hook fastener could also be formed by direct molding methods where either the final hook or a hook precursor is formed and subsequently treated to form the final hook form.

In certain applications, it has been discovered that very low hook densities are desirable. For example, hook densities of less than 100, preferably less than 70 and even less than 50 hooks per square centimeter are desirable when used to attach to low loft nonwovens using a relatively large area flexible hook fastener tab or patch. This low spacing has been found to increase the hooking efficiency of the individual hook elements, particularly relative to low cost and otherwise ineffective nonwoven materials not traditionally used as loop products. The hook tab or patch is also made flexible by suitable selection of the polymer forming the backing or base layer and/or by the stretching of the base layer reducing its thickness, to a preferred range of 30 μm to 60 μm. Biaxial orientation also reduces the hook density to the desired preferred range for a large area hook fastener. Generally, the fastener would be of a size of from 10 to 100 $cm^2$. When the fastener is less than 10 $cm^2$ the breathability becomes irrelevant and performance deteriorates due to the general low hook density. Fastener tabs greater than 100 $cm^2$ are difficult to handle by an end user and are less comfortable.

The large area breathable fastener forms a breathable closure system when is engaged to a large area mating surface which could be a breathable fibrous woven or nonwoven which in a garment application would preferably to joined to a breathable film or liquid barrier layer to keep liquids contained. The bonding of the fibrous layer to a breathable backing would be intermittent to ensure breathability of the end laminate. Such laminates are used extensively in disposable diapers or feminine hygiene products.

The large area fastener when used on a garment type application, such as diapers or the like, provides stability between the two engaged regions. The enlarged area provides resistance to twisting forces and therefore tends to keep the two engaged surfaces in a fixed relationship to each other. Further, when a large area fastener is brought forward or backward for engagement with an outer surface of an article, the large area fastener is capable of fastening into a large area of the outer surface of the article. With this, the need for a specific attachment region or target attachment zone can be eliminated if the garment can engage at some minimum level with the fastener. The larger area of the fastener also ensures secure closure due to the fastener's size. As such, large area breathable fasteners of the invention could potentially eliminate the need for a separate loop component or other "mating" fastener component on the breathable backing of the garment or article, otherwise provided with a fibrous type outer surface. The increased size of the large area fastener also can eliminate the need for secondary fasteners or bonded areas (such as passive bonds) that may be required to stabilize the overlapped regions of the article or garment.

Use of a large area fastener reduces the manufacturing complexity of a garment such as an absorbent article by eliminating the need for additional bond points or multiple fasteners to stabilize the fastening system of e.g., the front and rear waist regions. The addition of bond points or additional fasteners increases the complexity of the manufacturing process.

Specifically, in a preferred arrangement on a diaper (or like incontinent product) a large area hook fastener, is capable of directly engaging an outer surface of a diaper provided with a relatively low loft nonwoven without the need for an expensive loop patch. The large area breathable hook fastener can also prevent inadvertent disengagement of the diaper closure due to the large contact and attachment area creating a more stable garment closure. The oversized hook fastener could also be used in a prefastened pull-on type diaper type garments, due to the large area of fastener contact making the garment suitably stable for packaging and subsequent use.

Figure 4:
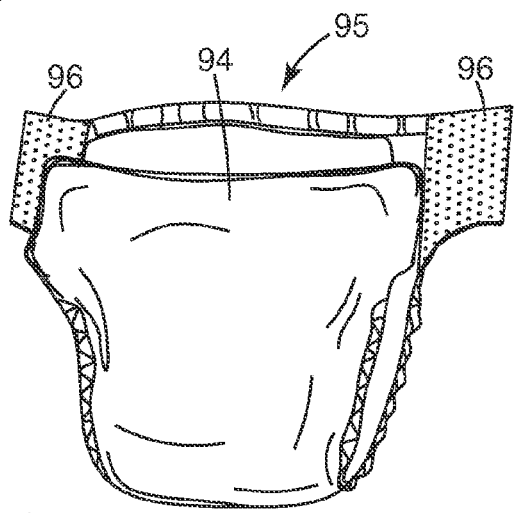
FIG. 4 is a perspective view of a disposable garment using a hook member according to the present invention.
Figure 5:
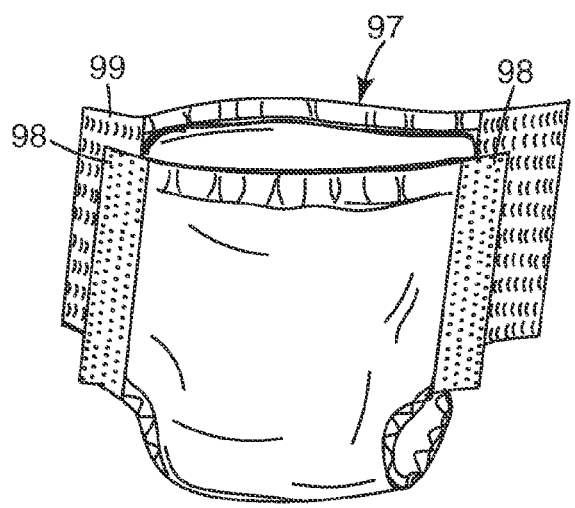
FIG. 5 is a perspective view of a disposable garment using a hook member according to the present invention.
Figure 6:
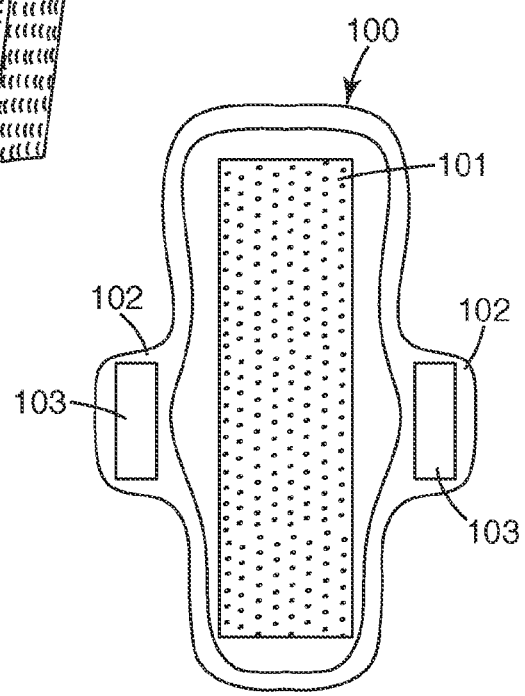
FIG. 6 is a perspective view of a feminine hygiene article using a hook member according to the present invention.

Examples of suitable uses for this large area hook fastener, as a hook tab or patch, are illustrated in FIGS. 3-6, 8 and 9. In FIG. 3, a large area breathable fastening tab is attached to a breathable carrier substrate 92 such as a nonwoven web, which is attached to a diaper 90 as is known in the art. The fastener tab could be of a size of from 10 to 100 cm$^2$, preferably 20 to 70 cm$^2$ and can be attached directly to a low loft nonwoven 94 forming the outer cover of the diaper 90. Typically, this low loft nonwoven would be a spunbond web, a bonded carded or air laid web, a spunlace web or the like. FIG. 4 is a variation of this fastening tab type construction for a diaper 95, however, where the hook tab 96 is directly bonded to the diaper 95, either at an ear cutout portion or at the edge region of the diaper. In the embodiments shown in FIGS. 3 and 4, the mating region could be a nonwoven used to form the nonwoven outer cover of the diaper or the nonwoven fluid permeable topsheet. FIG. 5 is a further embodiment of a large area hook tab 98 used with a pull up type diaper design. In this embodiment, the hook tab 98 would engage a suitable mating region 99 on the opposite face of the pull up diaper. Of course, these two elements could be reversed. FIG. 6 is an embodiment of the invention hook type fastener material being used as a large area patch 101 on a feminine hygiene article 100. The patch could be used as the primary attachment element to the undergarment, optionally a secondary attachment element 103 could be provided on attachment wings 102. The use of the low hook density hook fastener as a large area patch could also be used on a diaper where the patch could form a part or all of the diaper outer cover.

Figure 7:
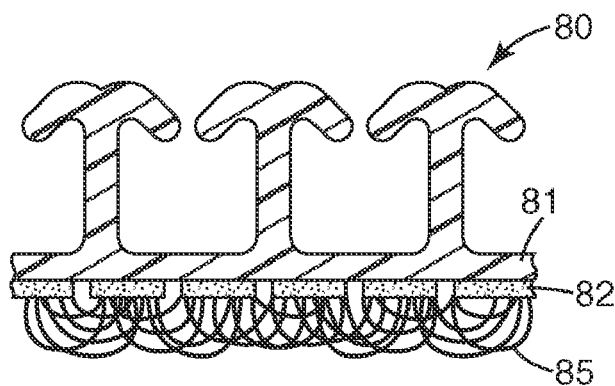
FIG. 7 is a breathable hook fastener of the present invention as a self-engaging structure.

FIG. 7 is an example of the large area fastener 80 provided with a loop material 85 on the face opposite that having the hook elements. The loop is a breathable type woven or nonwoven material and can be applied to the breathable backing 81 of the large area hook fastener 80 by intermittent bonding 82 which can be adhesive, heat or sonic bonding or the like so as not to unduly compromise the breathability of the backing 81. Breathable continuous adhesive layers are also possible.

Figure 8:
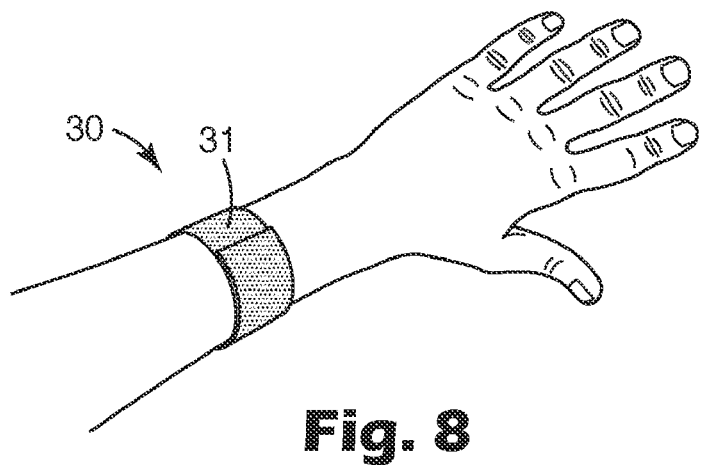
FIG. 8 is a breathable hook fastener of the present invention used as a body wrap.

This type of self-engaging fasteners 31 can be used as a wrap 30 such as shown in FIG. 8, for use as a sport wrap. The self-engaging fastener can also be used as a wrap for articles such as produce, where breathability would be beneficial.

Figure 9:
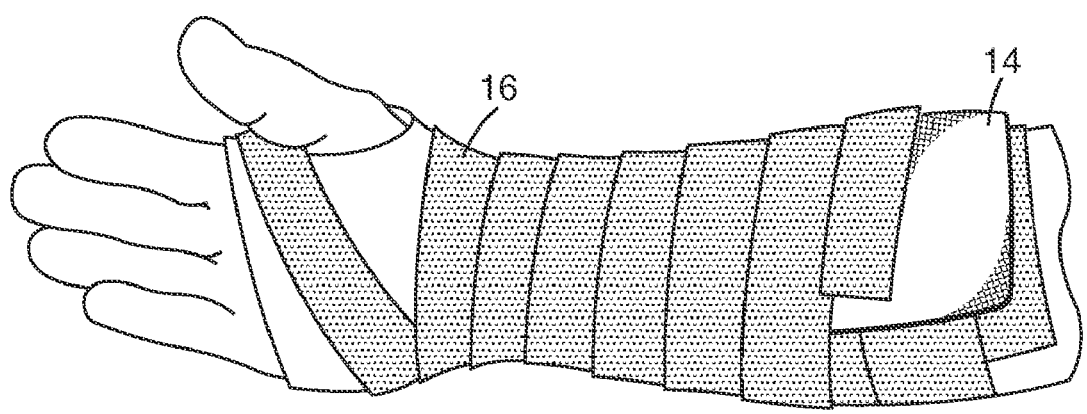
FIG. 9 is a breathable hook fastener of the present invention used as a body wrap.

FIG. 9 shows the self-engaging fastener 16 as a medical wrap which could be used with an absorbent pad 14, if desired, or use of the absorbent pad could be optional if the loop fabric was absorbent.

Test Methods

Gurley Time

The "Gurley" densometer or flowthrough time was measured on a densometer of the type sold under the trade designation "Model 4110" densometer by W. & L. E. Gurley of Troy, N.Y., which is calibrated and operated with a Gurley-Teledyne sensitivity meter (Cat. No. 4134/4135). The "Gurley" densometer time was determined in a manner similar to that specified in ASTM D726-58. "Gurley time" is the time it takes for 50 cc of air at 124 mm (4.88 in.) H2O pressure to pass through a sample of the web having a circular cross-sectional area of approximately 645 mm$^2$ (1 square inch). The testing was done at a temperature of approximately 23°-24° C. (74°-76° F.) and 50 percent relative humidity. Gurley time is usually inversely related to void volume of the hook fastener web. Gurley time is also usually inversely related to average pore size of the hook fastener web.

Compression Stiffness

A compression test was used to measure the stiffness of the webs of the invention. A sample was cut from the laminate, 25 mm wide by 60 mm long, the long direction being in the cross or transverse direction of the web. A cylinder was formed from this sample by bringing together the two ends, overlapping them by approximately 4 mm, and then stapling the two ends together. The cylindrical sample was then placed on a platen mounted to the lower jaw of an INSTRON Model 5500R constant rate of extension tensile machine. A plastic ring with a 45 mm outer diameter, 40 mm inner diameter and 5 mm thickness was then placed inside the cylindrical sample such that it rested on the platen. The ring serves as a shape retaining means as the sample cylinder is compressed. The upper jaw of the tensile machine was equipped with a flat compression plate. This plate was lowered at a rate of 10 mm/min. The load to compress the sample was continuously recorded. The peak recorded load, which represents the force required to buckle the sides of the sample cylinder, divided by the thickness of the base film of the web, is reported in kg/mm in Table 1 below as Compression Stiffness. 3 replicates were tested and averaged. Test sample replicates exhibiting multiple peaks were discarded.

Hook Dimensions

The dimensions of the Example and Comparative Example hook materials were measured using a Leica microscope equipped with a zoom lens at a magnification of approximately 25×. The samples were placed on an x-y moveable stage and measured via stage movement to the nearest micron. A minimum of 3 replicates were used and averaged for each dimension.

Comparative Example 1

A mechanical fastener hook web was made using apparatus similar to that shown in FIG. 1. A blend of 99% polypropylene/polyethylene impact copolymer (SRC-104, 1.5 MFI, Dow Chemical Corp., Midland, Mich.) and 1% white color concentrate (15100P 50:50 PP/TiO2, Clariant Corp., Minneapolis, Minn.) was extruded with a 6.35 cm single screw extruder (24:1 L/D) using a barrel temperature profile of 177° C.-232° C.-246° C. and a die temperature of approximately 235° C. The extrudate was extruded vertically downward through a die equipped with a die lip having an opening cut by electron discharge machining. After being shaped by the die lip, the extrudate was quenched in a water tank at a speed of 6.1 meter/min with the water being maintained at approximately 10° C. The resulting structure had a profile similar to that shown in FIG. 2. The web was then advanced through a cutting station where the ribs (but not the base layer) were transversely cut at an angle of 23 degrees measured from the transverse direction of the web. The spacing of the cuts was 305 microns. There were approximately 10 rows of ribs or cut hooks per centimeter. The base film layer had a thickness of approximately 240 microns. The width of the individual hook elements was approximately 500 microns as measured in the cross-direction of the web. A 115 mm by 115 mm piece of the web was then mounted into the frame of a KARO IV (Bruckner Gmbh, Siegfred, Germany) pantograph stretcher (providing a stretchable area of 100 mm by 100 mm) and then preheated at 130° C. for 60 seconds. The sample was then stretched biaxially at a rate of 100%/sec to a dimension of 200 mm by 200 mm.

Example 1

A mechanical fastener hook web was made as in Comparative Example 1 except a precompounded (twin screw) blend of 65% polypropylene (5D45, 0.65 MFI, Dow Chemical, Midland, Mich.), 35% mineral oil (White Mineral Oil #31 USP Grade Amoco Oil Company) and 0.06% dibenzylidene sorbitol nucleating agent (Millad 3905, Milliken Chemical Co., Spartanburg, N.C.) was extruded with a 6.35 cm single screw extruder (24:1 L/D) using a gradually increasing barrel temperature profile of 177° C. in the first zone to a temperature of 260° C. in the last zone and a die temperature of approximately 260° C. After being shaped by the die lip, the extrudate was quenched in a water tank at a speed of 6.1 meter/min with the water being maintained at approximately 45° C. The web was then advanced through a cutting station where the ribs (but not the base layer) were transversely cut at an angle of 23 degrees measured from the transverse direction of the web. The spacing of the cuts was 305 microns. There were approximately 10 rows of ribs or cut hooks per centimeter. The base film layer had a thickness of approximately 127 microns. The width of the individual hook elements was approximately 500 microns as measured in the cross-direction of the web. A 115 mm by 115 mm piece of the web was then mounted into the frame of a KARO 4 pantograph stretcher (providing a stretchable area of 100 mm by 100 mm) and then preheated at 130° C. for 60 seconds. The sample was then stretched biaxially at a rate of 100%/sec to a dimension of 200 mm by 200 mm. The resulting oriented film was opaque and microporous as evidenced by the Gurley Time test described above.

Table 1 below shows the dramatic decrease in stiffness and increase in porosity of the microporous webs as compared to the non-porous webs. The Gurley Time of web C1 could not be measured as no air was able to pass through the sample.

TABLE 1

| Example | Compression Stiffness (kg/mm) | Gurley Time (sec) | Porosity (cm³) |
|---------|-------------------------------|-------------------|----------------|
| C1      | 15.1                          | —                 | 0              |
| 1       | 2.3                           | 21.1              | 0.000375       |

What is claimed is:

1. A breathable fastening system comprising:
a breathable mechanical fastener surface; and
a large area breathable fastener comprising a breathable film backing having an upper surface and a lower surface and a multiplicity of spaced projections projecting from at least the upper surface of the breathable film backing, each projection comprising a stem portion directly attached at one end to the breathable film backing and separated from neighboring projections by the breathable film backing, the breathable film backing having a porosity of from 0.0001 to 0.005 cm$^3$, a backing thickness of from 25 to 200 µm, a stiffness of from 10 to 2000 Gurley stiffness units and a projection containing surface area of at least 10 cm$^2$.

2. The breathable fastening system of claim 1 wherein the hacking thickness of the large area fastener is from 50 to 150 microns.

3. The breathable fastening system of claim 1 wherein the large area breathable fastener has a stiffness of from 10 to 200 Gurley stiffness units.

4. The breathable fastening system of claim 1 wherein the backing thickness is from 50 to 150 microns and the stiffness is from 10 to 200 Gurley stiffness units.

5. The breathable fastening system of claim 1 wherein the spaced projections are hooks and the hook containing surface area is from 20 to 70 cm$^2$.

6. The breathable fastening system of claim 1 wherein the spaced projections are hooks and hook density is at least 50 hooks/cm$^2$.

7. The breathable fastening system of claim 6 wherein the hook density is from 70 to 300 hooks/cm$^2$.

8. The breathable fastening system of claim 1 wherein the spaced projections are hooks and the hook density is less than 100 hooks/cm$^2$.

9. The breathable fastening system of claim 8 wherein the hod: density is less than 50 hooks/cm$^2$.

* * * * *

UNITED STATES PATENT AND TRADEMARK OFFICE
CERTIFICATE OF CORRECTION

PATENT NO. : 7,748,090 B2  Page 1 of 1
APPLICATION NO. : 11/612082
DATED : July 6, 2010
INVENTOR(S) : Jayshree Seth It is certified that error appears in the above-identified patent and that said Letters Patent is hereby corrected as shown below:

Col. 8, line 33, please delete "lowerjaw" and insert --lower jaw--.

Col. 10, line 51, Claim 9, please delete "hod:" and insert --hook--.

Signed and Sealed this

Nineteenth Day of October, 2010

David J. Kappos
*Director of the United States Patent and Trademark Office*